(12) United States Patent
Hloucha et al.

(10) Patent No.: US 9,656,104 B2
(45) Date of Patent: May 23, 2017

(54) USE OF MICROEMULSIONS IN COSMETIC CLEANING COMPOSITIONS

(75) Inventors: Matthias Hloucha, Köln (DE); Esther Küsters, Erkrath (DE); Jasmin Schorb, Monheim (DE); Daniela Prinz, Dormagen (DE); Werner Seipel, Hilden (DE); Michaela Wirtz, Langenfeld (DE)

(73) Assignee: Cognis IP Management GmbH, Düsseldorf (DE)

( * ) Notice: Subject to any disclaimer, the term of this patent is extended or adjusted under 35 U.S.C. 154(b) by 436 days.

(21) Appl. No.: 14/131,392

(22) PCT Filed: Jun. 15, 2012

(86) PCT No.: PCT/EP2012/061425
§ 371 (c)(1),
(2), (4) Date: Apr. 11, 2014

(87) PCT Pub. No.: WO2013/007473
PCT Pub. Date: Jan. 17, 2013

(65) Prior Publication Data
US 2014/0219946 A1  Aug. 7, 2014

Related U.S. Application Data

(60) Provisional application No. 61/505,563, filed on Jul. 8, 2011.

(30) Foreign Application Priority Data

Jul. 8, 2011 (EP) .................................. 11005589

(51) Int. Cl.
| | | |
|---|---|---|
| A61K 8/73 | (2006.01) |
| A61Q 19/00 | (2006.01) |
| A61K 8/06 | (2006.01) |
| A61K 8/34 | (2006.01) |
| A61K 8/60 | (2006.01) |
| A61Q 5/02 | (2006.01) |
| A61Q 19/10 | (2006.01) |
| A61K 8/37 | (2006.01) |
| A61Q 1/14 | (2006.01) |
| A61Q 5/12 | (2006.01) |

(52) U.S. Cl.
CPC ............ *A61Q 19/007* (2013.01); *A61K 8/068* (2013.01); *A61K 8/345* (2013.01); *A61K 8/375* (2013.01); *A61K 8/604* (2013.01); *A61Q 1/14* (2013.01); *A61Q 5/02* (2013.01); *A61Q 5/12* (2013.01); *A61Q 19/10* (2013.01)

(58) Field of Classification Search
CPC ...... A61K 8/604; A61K 2800/21; A61K 8/06; A61K 8/31; A61K 8/602
See application file for complete search history.

(56) References Cited

U.S. PATENT DOCUMENTS

| 5,980,874 A | 11/1999 | Foerster et al. |
| 6,303,109 B1 | 10/2001 | Foerster et al. |
| 6,468,551 B1 | 10/2002 | Diec et al. |
| 6,607,733 B1 | 8/2003 | Diec et al. |
| 8,715,631 B2 * | 5/2014 | Araujo ..................... A61Q 5/02 424/70.1 |
| 2007/0160652 A1 | 7/2007 | Mueller |
| 2010/0247588 A1 | 9/2010 | Hloucha et al. |
| 2010/0311627 A1 | 12/2010 | Hloucha et al. |
| 2012/0027826 A1 | 2/2012 | Strauss |

FOREIGN PATENT DOCUMENTS

| DE | 3534733 | 4/1987 |
| DE | 19903717 | 8/2000 |
| DE | 102007020426 | 10/2008 |
| EP | 1767554 | 3/2007 |
| EP | 2340804 | 7/2011 |
| FR | 2252840 | 6/1975 |
| GB | 1494916 | 12/1977 |
| JP | 2005-046841 A | 2/2005 |
| JP | 2007-523107 A | 8/2007 |
| WO | WO-98/15255 | 4/1998 |
| WO | WO-98/40044 | 9/1998 |
| WO | WO-99/48473 | 9/1999 |
| WO | WO-2008/155074 | 12/2008 |
| WO | WO-2008/155075 | 12/2008 |
| WO | WO-2009/029046 | 3/2009 |

OTHER PUBLICATIONS

"English Machine Translation of DE19903717—Cited in PCT Search Report", Aug. 3, 2000, 13 pages.
"PCT International Search Report for PCT/EP2012/061425", Aug. 14, 2013, 5 pages.

* cited by examiner

*Primary Examiner* — Nannette Holloman
(74) *Attorney, Agent, or Firm* — Marshall, Gerstein & Borun LLP

(57) ABSTRACT

Provided are microemulsions comprising: (a) at least one alkyl (oligo)glycoside, (b) at least one cosurfactant different from (a), (c) at least one non-water-soluble organic oil component, (d) at least one moisturizing agent, (e) and water. These microemulsions may be used for producing cleaning compositions and also cosmetic cleaning compositions, comprising: (A) any microemulsion provided herein, (B) one or more anionic surfactants, (C) one or more cationic polymers; (D) optionally further surfactants; (E) optionally cosmetic additives, and (F) water.

13 Claims, No Drawings

USE OF MICROEMULSIONS IN COSMETIC CLEANING COMPOSITIONS

CROSS-REFERENCE TO RELATED APPLICATIONS

This application is the national stage entry of PCT/EP2012/061425, filed on Jun. 15, 2012, which claims priority to European Patent application number 11005589.4, filed on Jul. 8, 2011 and U.S. Provisional application No. 61/505,563 filed Jul. 8, 2011, all of which are incorporated herein by reference in their entireties.

FIELD

The invention is in the field of cosmetic cleaning compositions which are present in the form of finely divided emulsions based on oil-containing microemulsions and further relates to microemulsions for producing cosmetic cleaning compositions such as shower gels.

BACKGROUND

Cleaning compositions are generally emulsions of greater or lesser concentration which, as is known, comprise in particular surfactants and care substances as well as oil components. On the part of the consumer, there is the desire for those preparations which are not only particularly skin-friendly, but remove especially oily soilings—in the widest sense also decorative cosmetics—rapidly and residue-free. In many cases, the manufacturer of such end preparations will refrain from mixing the individual feed materials itself; it will rather attempt to fall back on so-called "all-purpose compounds". These are understood as meaning mixtures which can serve as the basis for very different end products. These mixtures are being increasingly supplied as microemulsions with diverse advantages. In the simplest case, the concentrated microemulsions are diluted to the application concentration by adding water and then themselves constitute the compositions. As a rule, however, they will be added with appropriate additives. Depending on the field of use of these "all-purpose compounds" in the form of a microemulsion, different requirements are set which, in the best case, are already satisfied by the microemulsion. In individual cases, further components have to be added which meet these requirements without destroying the positive features of the microemulsion.

In the area of application of cosmetic cleaning compositions such as, for example, shower gels, use is usually made of concentrated aqueous surfactant solutions, on which a whole series of sometimes very different requirements are nowadays placed. The compositions should have the highest possible content of active substance,
at the same time be liquid or at least flowable,
have the lowest possible low-temperature cloud point,
be dermatologically acceptable, i.e. non skin-irritating, even in concentrated form,
be storage-stable,
contain the fewest possible additives such as, for example, preservatives.

The point relating to dermatological acceptability deserves particular attention since consumer expectations have risen in recent years in this respect. Against the background of an increasing number of consumers who have sensitive skin, compositions which have advantageous properties in this regard are becoming more and more important. Consequently, it was an important part of the object to provide compositions which comprise the fewest possible preservatives. This allows the buyer and end-product manufacturers furthermore to incorporate preferred preservatives and additives of choice into the end product.

Although there is a large number of skin-friendly cleaning compositions on the market, there is nevertheless an intense interest, both by the raw material suppliers and the manufacturers, to find compositions which better satisfy the required objective than the products of the prior art. This applies in particular with regard to the simplest possible production method for such compositions.

After washing, skin and hair often feel rough and brittle, particularly if they have already been damaged by environmental influences. Moreover, hair can also be damaged by coloring or perming and is then often characterized by a dry, straw-like feel after hair washing.

It is therefore the aim of the cosmetic cleaning compositions to compensate for the loss of sebum and water in skin and hair that is caused by daily washing. The body care products should protect against environmental influences, in particular against sun and wind, and delay skin aging.

For this reason, conditioners are often used in shampoo compositions which are supposed to counteract these disadvantages. Shampoo compositions are therefore often found which comprise silicones as conditioners. However, these can attach irreversibly to the hair and in so doing for their part cause negative effects on the feel, in the worst case even problems during the coloring and perming of hair.

In many cosmetic preparations, oils and waxes are suitable as conditioning agents. However, these are nowhere near as marked in their effect as silicones. These oils and waxes can hitherto only be stabilized in the preparations in small amounts.

WO 2008155075 describes cosmetic preparations which comprise a microemulsion and at least one cationic polymer alongside non-alkoxylated surfactants. These preparations are used as conditioning agents in shampoo and hair treatment compositions.

A disadvantage of the microemulsions of the prior art is the low storage stability and often the problem of incorporation into the cleaning composition formulation without heating.

When providing microemulsions with anionic, cationic or amphoteric surfactants, it is also problematic that the oil components can be used only with very great difficulty since the surfactants are often too water-soluble and therefore scarcely have emulsifying properties.

DE 3534733 describes microemulsions, although the fraction of the solubilized oil components in the range from 0.5 to 3% by weight is low. The problem of incorporating larger amounts of oil also becomes clear in WO 9948473; here, the incorporation of just 0.5-1% by weight of oil is discussed.

It is known that oil-in-water emulsions which are prepared with nonionic emulsifiers often suffer from phase inversion upon heating, i.e. at elevated temperatures, the external, aqueous phase can become the internal phase. This process is generally reversible, meaning that, upon cooling, the original emulsion type is reformed again. Emulsions which have been prepared above the phase inversion temperature generally have a low viscosity and high storage stability.

For example, WO 98/40044 describes aqueous preparations of water-soluble surfactants which have lipid-surfactant mixed micelles with an average particle size of below 500 nm and thus appear bluish-white. The subject matter of WO 98/15255 is microemulsion gels of the oil-in-water type in which the oil droplets are stabilized in the water phase by associative thickeners.

SUMMARY

Provided are microemulsions comprising: (a) at least one alkyl (oligo)glycoside, (b) at least one cosurfactant different from (a), (c) at least one non-water-soluble organic oil component, (d) at least one moisturizing agent, (e) and water. These microemulsions may be used for producing cleaning compositions and also cosmetic cleaning compositions, comprising: (A) any microemulsion provided herein, (B) one or more anionic surfactants, (C) one or more cationic polymers; (D) optionally further surfactants; (E)optionally cosmetic additives, and (F) water.

The object of the present invention was therefore to provide microemulsions and cosmetic cleaning compositions which better satisfy the required objects than known products, the cleaning behavior of which corresponds to the prior art, or in the best case even surpasses this, and which leave behind a pleasant skin feel following application to the skin. On the skin, a feeling of soft, richly cared for skin should be formed, and any cleaned hair should be given a pleasant feel without a greasy feel being left behind.

It is a further object of the present invention to provide oil-containing cleaning products which can be applied to the skin in a sensorily pleasant manner, distributed and washed off, with the skin care oil phase remaining on the skin. Furthermore, the compositions should leave behind a long-lasting care and pleasant skin feel without losing the cleaning effect during the rinsing operation. The aim was to provide rinse-off products which have a refatting effect and do not adversely affect the moisture content of the skin.

The cleaning composition should comprise microemulsions which can be easily formulated, are stable over a prolonged period and already include the property of conveying a pleasant skin feel.

Furthermore, cosmetic hair care compositions should be provided, the conditioning performance of which corresponds to that of silicone-containing preparations or, in the best case, even surpasses this.

DETAILED DESCRIPTION

It has now been found that certain microemulsions are able to achieve the object set above.

It could not have been foreseen by the person skilled in the art that the object could be achieved through a microemulsion and/or by a finely divided emulsion which comprises this microemulsion which is characterized by the mixing of surfactant, cosurfactant, organic oil phase and moisturizing agent.

Thanks to the microemulsion, this cleaning composition component is present in the form of a low viscosity composition and can be incorporated very readily into any type of cleaning and care composition, such that transparent or slightly cloudy products can be produced. Preference is given to the use as cosmetic cleaning composition in shower gel formulations or shampoo preparations. Consequently, the preferred use in combination formulations for skin and hair (two in one products) is also obvious. It was possible to show that a microemulsion comprising a high concentration of oil bodies and glycerol as moisturizing agent exhibits excellent properties as cosmetic cleaning composition in body care because the combination of these two substances leads to the fact that a pleasant long-lasting care skin feel can be felt. The two substances lead in their combination to a long-lasting adhesion to skin and hair but without being greasy and/or leaving behind an unpleasant greasy feel since they are present in the microemulsion in incorporated form. This effect was demonstrated by deposition tests. For a shower gel formulation, it is also highly advantageous that a microemulsion based on oils in combination with a high concentration of moisturizing agents significantly improves the skin feel after the showering process. This was demonstrated in sensory tests.

A further advantage of the microemulsion according to the invention is that it is preferably free from alkoxylated compounds and can thus also be incorporated into cosmetic products, for which the consumer attaches increased importance to "green cosmetics".

The microemulsion according to the invention is, furthermore, preferably free from added silicones.

Through the use of large amounts of oil bodies and the combination with high concentrations of moisturizing agents, preferably glycerol, it is possible to use more oil than water and, as a result, to save on adding a preservative. The small fraction of water does not make the addition of preservative absolutely necessary without, however, reducing the storage stability.

A first subject matter of the present application is a microemulsion comprising
(a) at least one alkyl (oligo)glycoside,
(b) at least one cosurfactant different from (a),
(c) at least one non-water-soluble organic oil component,
(d) at least one moisturizing agent, and
(e) water.

Furthermore, optionally further ingredients are also possible, such as biocides, pH regulators, dyes, antifoams, preservatives or perfumes as component (f). When used for producing cosmetic cleaning compositions, as further ingredients, preference is given to cosmetic additives, which are described in more detail later.

The microemulsion according to the invention can be used in the form of or as dilute solution. For use in cosmetic cleaning compositions such as shampoo, baby care products, foam bath, bath oil, the microemulsion can be used directly or be formulated with customary additives such as foam formers, thickeners, cationic polymers, preservatives, active ingredients. For the use as shower gel, the addition of foam formers and thickeners is preferred, in order to obtain a gel-like consistency. For the use as impregnating agent for flat structures, a dilution with water is preferred.

In a preferred embodiment, a microemulsion is used, comprising:
a) 1-35% by weight of at least one alkyl (oligo)glycoside,
b) 1-20% by weight of at least one cosurfactant different from (a),
c) 20-60% by weight of an organic oil phase,
d) 6-15% by weight of at least one moisturizing agent,
e) water, and
f) 0-5% by weight of further ingredients
with the proviso that the sum of (a) to (f) gives 100% by weight.

In a particularly preferred embodiment, a microemulsion is used for producing cosmetic cleaning compositions, comprising:
a) 8-30% by weight of at least one alkyl (oligo)glycoside,
b) 10-20% by weight of at least one cosurfactant different from a),
c) 20-50% by weight of an organic oil phase, preferably comprising ester oils,
d) 8-11% by weight of at least one moisturizing agent e) water,
f) 0-5% by weight of further ingredients,
with the proviso that the sum of (a) to (f) gives 100% by weight.

The microemulsion which is used for producing cosmetic cleaning compositions consists particularly preferably of a) to f) in the quantitative ratios specified in the paragraph above.

According to the invention, the particles are present in finely divided form in the microemulsion or in the cosmetic cleaning and care compositions. Within the context of the invention, "finely divided" means an average particle size of preferably less than 100 nm, specifically 3 to 50 nm, for the particles in the microemulsion. Upon dilution of the microemulsion the average particle size in the resulting diluted product can be up to 5000 nm. The particle size is determined in accordance with the DLS method using an instrument called Horiba LB-500.

Microemulsion

Microemulsions are known per se. Microemulsions are macroscopically homogeneous, optically transparent, low viscosity, thermodynamically stable mixtures. Depending on the type of surfactant used, the microemulsion exhibits a temperature-dependent phase behavior. Particularly some nonionic surfactants, and here in particular surfactants whose hydrophilic molecular moieties are formed from ethoxy or propoxy groups, lead to a characteristic temperature-dependent phase behavior in microemulsions.

A prerequisite for the formulation of microemulsions is an extremely low interfacial tension between the water-rich and the oil-rich phase. For the microemulsions, this can assume values between $10^{-1}$ and $10^{-5}$ $mNm^{-1}$.

The average particle sizes of the microemulsions are usually below 100 nm, preferably between 3 and 50 nm. They have a high transparency and are stable against visible phase separation upon centrifugation at 2000 rpm for at least 30 minutes. The microemulsions within the context of the present teaching preferably exhibit an average particle size of less than 100 nm. The conductivity of the microemulsions according to the invention is preferably in the range greater than/equal to 200 μSi/cm and particularly preferably greater than/equal to 400 μSi/cm.

A preferred range is 400 to 1200 μSi/cm. The microemulsions according to the invention are preferably transparent, in particular they exhibit a transparency greater than/equal to 80% at 40° C., with transparency values greater than 90% at 40° C. being typical. Preference is given to those microemulsions which have a transparency, measured at 40° C., of 95 to 100%.

The microemulsions are preferably produced simply by mixing the oil phase with the further oil-soluble ingredients, heating the oil phase to above the melting point of all of the constituents and subsequently adding the aqueous surfactant-containing phase. Alternatively, the heated oil phase can also be added to the aqueous phase. The thermodynamically stable microemulsion is then formed spontaneously, additionally with stirring if necessary.

Component (a)

As component (a) of the present invention, preference is given to using microemulsions based on alkyl (oligo)glycosides.

Alkyl and alkenyl oligoglycosides are known nonionic surfactants which conform to the general formula (I),

$$R^1O-[G]_p \qquad (I)$$

in which $R^1$ is an alkyl and/or alkenyl radical having 4 to 22 carbon atoms, G is a sugar radical having 5 or 6 carbon atoms and p is numbers from 1 to 10. They can be obtained by the relevant methods of preparative organic chemistry. The alkyl and/or alkenyl oligoglycosides can be derived from aldoses or ketoses having 5 or 6 carbon atoms, preferably glucose. The preferred alkyl and/or alkenyl oligoglycosides are thus alkyl and/or alkenyl oligoglucosides. The index number p in the general formula (I) indicates the degree of oligomerization (DP), i.e. the distribution of mono- and oligoglycosides, and is a number between 1 and 10. Whereas p in any given compound must always be a whole number and here in particular can assume the values p=1 to 6, the value p for a specific alkyl oligoglycoside is an analytically determined calculated parameter which, in most cases, is a fractional number. Preference is given to using alkyl and/or alkenyl oligoglycosides with an average degree of oligomerization p of from 1.1 to 3.0. From the point of view of application, preference is given to those alkyl and/or alkenyl oligoglycosides whose degree of oligomerization is less than 1.7 and in particular is between 1.2 and 1.4. The alkyl or alkenyl radical $R^1$ can be derived from primary alcohols having 4 to 22, preferably 10 to 16, carbon atoms. Typical examples are butanol, caproic alcohol, caprylic alcohol, capric alcohol and undecyl alcohol, and also technical-grade mixtures thereof, as are obtained for example during the hydrogenation of technical-grade fatty acid methyl esters or in the course of the hydrogenation of aldehydes from the Roelen oxo synthesis. Preference is given to alkyl oligoglucosides of chain length $C_{10}$-$C_{16}$ (DP=1 to 3). Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachidyl alcohol, gadoleyl alcohol, behenyl alcohol, erucyl alcohol, brassidyl alcohol, and also technical-grade mixtures thereof. Preference is given to alkyl oligoglucosides based on hydrogenated $C_{12-14}$-coconut alcohol with a DP of from 1 to 3.

The microemulsions within the context of the present teaching comprise component (a) preferably in amounts of from 1 to 35% by weight, based on the total weight of the microemulsion. For the use for producing cosmetic cleaning compositions, amounts of from 8 to 30% by weight, particularly preferably from 15 to 25% by weight, based on the total weight of the microemulsion, are present.

Component (b) Cosurfactant

As a further obligatory component, the microemulsions comprise at least one cosurfactant, which must be structurally different from component (a) and is a polyol fatty acid ester. Within the context of the invention, polyols include polyols whose fatty acid esters are used as cosurfactants, alcohols with at least 3 carbon atoms and at least three hydroxyl groups.

For producing cosmetic cleaning compositions, preferred cosurfactants are fatty acid esters of polyols which are selected from the group which is formed from sugar esters, W/O emulsifiers such as sorbitan esters, sorbitol partial esters, polysorbates, polyglyceryl esters, polyglyceryl partial esters, specifically, for example, polyglyceryl-2 dipolyhydroxystearate, polyglyceryl-3 diisostearate.

Furthermore, preference is given to mono- and dihydric alcohols of linear or branched alkanes. For the production of cosmetic cleaning compositions, the cosurfactants are preferably present in amounts of 1-20% by weight, particularly preferably in amounts of 10-20% by weight, based on the total weight of the microemulsion.

The cosurfactants can also be used as a mixture. In the mixture, the amounts of cosurfactants are based on the sum of the cosurfactants used. Preference is given to using identical parts of different cosurfactants in the mixture, based on the % by weight in the microemulsion.

Component (c) Organic Oil Phase

The microemulsions within the context of the present teaching comprise, as further obligatory constituent, a water-insoluble so-called oil phase which comprises at least one oil component, i.e. a non-water-soluble organic phase. Preferably in amounts of from 20 to 60% by weight, based on the total weight of the microemulsion.

Preferably, the microemulsions comprise water-insoluble oil components or oil phases selected from the group of Guerbet alcohols based on fatty alcohols having 6 to 18 carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, esters of linear $C_6$-$C_{22}$-fatty acids with branched alcohols, esters of $C_6$-$C_{22}$-fatty alcohols and/or Guerbet alcohols with aromatic carboxylic acids, triglycerides based on $C_6$-$C_{10}$-fatty acids, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, Guerbet carbonates based on fatty alcohols having 6 to 18, preferably 8 to 10, carbon atoms, esters of benzoic acid with linear and/or branched $C_6$-$C_{22}$-alcohols, linear or branched, symmetrical or asymmetrical dialkyl ethers having 6 to 22 carbon atoms per alkyl group, aliphatic or naphthenic hydrocarbons and dialkylcyclohexanes.

For the use for producing cosmetic cleaning compositions, the water-insoluble oil component is used preferably in amounts of 20-60% by weight, preferably 20 to 50% by weight, of active substance, based on the total weight of the microemulsion. For cosmetic cleaning compositions, preferred organic oil phases, with the exception of alkoxylated compounds, are liquid ester oils, i.e. esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, esters of linear $C_6$-$C_{22}$-fatty acids with branched alcohols, esters of $C_{18}$-$C_{38}$-alkylhydroxycarboxylic acids with linear or branched $C_6$-$C_{22}$-fatty alcohols, esters of linear and/or branched fatty acids with polyhydric alcohols and/or Guerbet alcohols, esters of $C_6$-$C_{22}$-fatty alcohols and/or Guerbet alcohols with aromatic carboxylic acids. Furthermore triglycerides based on $C_6$-$C_{10}$-fatty acids, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, linear and branched $C_6$-$C_{22}$-fatty alcohol carbonates.

Particular preference is given to ester oils selected from the group which is formed from isopropyl palmitate, isopropyl myristate, ethylhexyl palmitate, ethylhexyl stearates, di-n-octyl carbonates, caprylyl caprylate, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate, dioctyl malate, propylene glycol dimerdiol or trimertriol or mixtures thereof. Of these ester oils, particular preference is given to caprylyl caprylate, cococaprylate and dialkyl carbonates.

The organic oil phase for cosmetic cleaning compositions particularly preferably consists of liquid oils, preferably of liquid ester oils. As a result of the absence of solid fats and/or waxes, the storage stability of the microemulsion can be increased. Consequently, it is preferred according to the invention to produce, and to use, the microemulsion free from waxes or solid fats. As by-products, traces of these fats or waxes may always be present in the other constituents, although it is preferred to formulate the microemulsion without the addition of these fats and waxes.

Hydrocarbons is the term used to refer to organic compounds which consist only of carbon and hydrogen. They include both cyclic and acyclic (=aliphatic) compounds. They include both saturated and mono- or polyunsaturated compounds. The hydrocarbons may be linear or branched. Depending on the number of carbon atoms in the hydrocarbon, the hydrocarbons can be divided into odd-numbered hydrocarbons (such as for example, nonane, undecane, tridecane) or even-numbered hydrocarbons (such as, for example, octane, dodecane, tetradecane). Depending on the type of branching, the hydrocarbons can be divided into linear (=unbranched) or branched hydrocarbons. Saturated, aliphatic hydrocarbons are also referred as to paraffins.

Component (d)—Moisturizing Agent

A further obligatory constituent of the microemulsion and of the cosmetic cleaning composition is at least one moisturizing agent. The term moisturizing agent is used here synonymously for humectants or wetting agent or hydrotropes. The moisturizing agents ensure a pleasant skin feel after cleaning and return to the skin a moisture which is reduced by cleaning active ingredients in the "rinse-off" products.

A further advantage of large amounts of moisturizing agent leads to the effect that no and/or only small amounts of preservatives have to be used since the water fraction is preferably smaller than the oil fraction. In principle, all known moisturizing agents can be used. The moisturizing agents are preferably selected from the group which is formed from acetyl hexapeptide-8, acetyl histidine, beta-alanine, ammonium lactate, 1,2-butanediol, 2,3-butanediol, butyl-ethyl propanediol, deoxyglutamyl-fructose, diglycerol, fructan fructooligosaccharides, fructose, glucamine, alpha-glucan, alpha-glucan oligosaccharide-1, glucose, glucose glutamate, glucose pentaisovalerate, glucuronic acid, glucuronolactone, glutamic acid, glycerol, lactose, maltitol, maltose, mannitol, mannose, polyglycerol-3, polyglycerol-4, polyglycerol-6, polyglycerol-10, polyglycerol-20, polyglycerol-40, sorbitol, xylitol, xylose.

Glycerol is particularly preferred as moisturizing agent. The moisturizing agent is used in amounts of 6-15% by weight in the microemulsion used for producing the cosmetic cleaning composition. Particular preference is given to the use of 8-11% by weight of moisturizing agent.

Component (e) Water

A further essential constituent of the microemulsions and of the cosmetic composition is water. The water should preferably be demineralized. The microemulsions preferably comprise up to 45% by weight of water.

For the cosmetic cleaning compositions, the preferred water fraction is greater than 80% by weight, based on the total amount of the cosmetic cleaning compositions. This means that the fraction of water from the microemulsion present is included in the 80% by weight. Likewise, water from the other ingredients, which are never free from water, is included.

Further Ingredients (f)

In addition, the microemulsions can comprise further ingredients as additional component (f), for example a cationic compound, in particular quaternary ammonium compounds or a cationic polymer. Quaternary ammonium compounds are understood here as meaning in particular quaternized fatty acid triethanolamine ester salts. Likewise of suitability are, however, alkylammonium halides.

Suitable cationic polymers are, for example, cationic cellulose derivatives, such as e.g. a quaternized hydroxyethylcellulose, cationic starch, copolymers of diallylammonium salts and acrylamides, quaternized vinylpyrrolidone/vinylimidazole polymers, such as, e.g. Luviquat (BASF), condensation products of polyglycols and amines, quaternized collagen polypeptides, such as, for example, lauryldimonium hydroxypropyl hydrolyzed collagen (Lamequat), quaternized wheat polypeptides, polyethyleneimine, copolymers of adipic acid and dimethylaminohydroxypropyldiethylenetriamine (cartaretine), copolymers of acrylic acid with dimethyldiallylammonium chloride (Merquat 550), polyaminopolyamides, as described e.g. in FR-A 2252840, and also their crosslinked water-soluble polymers, cationic chitin derivatives, such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, quaternized ammonium salt polymers, such as e.g. Mirapol A-15, Mirapol AD-1, Mirapol AZ-1 from Miranol.

Further preferred cationic polymers are selected from the group of homopolymers or copolymers of ester or amide derivatives of acrylic acid or methacrylic acid (e.g. INCI: Polyquaternium-7 or PQ-7), homopolymers of methacryloyl-ethyltrimethylammonium chloride (INCI: Polyquaternium-37 or PQ-37), quaternary copolymers of hydroxyethylcellulose and diallyldimethylammonium chloride (INCI: Polyquaternium-4 or PQ-4), polymeric quaternized ammonium salts of hydroxyethylcellulose modified with a trimethylammonium-substituted epoxide (INCI: Polyquaternium-10 or PQ-10), depolymerized guar gum derivatives which are quaternized (INCI: Guar Hydroxypropyl Trimonium Chloride) or quaternized guar derivatives and quaternary copolymers of hydroxyethyl-cellulose and diallyldimethylammonium chloride. In a preferred embodiment, the cationic polymer is selected from the group which is formed from Polyquaternium-7, Polyquaternium-10 and cationic guar derivatives.

Furthermore, cationic polymers according to the teaching of EP 1 767 554 A1 can advantageously be used, which are sold by the applicant under the name Polyquart Pro. The microemulsions according to the invention preferably comprise 0.05 to 2% by weight of these cationic polymers.

The cosmetic cleaning compositions according to the invention comprise as component C) the specified cationic polymers. Here too, the preferred cationic polymers are selected from the group which is formed from Polyquaternium-7, Polyquaternium-10 and cationic guar derivatives. In a particularly preferred embodiment, preference is given to cationic guar derivatives since these are in keeping with the "green" concept.

Moreover, possible optional further ingredients for the microemulsion are those which are selected from the group which is formed from pH regulators such as citric acid or phenoxyethanol, UV photoprotective filters, antioxidants, biogenic active ingredients, perfume, dyes, biocides, antifoams and preservatives, and also alcohols such as ethanol, isopropanol and/or propanol.

These optional components are present in the microemulsion in total preferably in amounts of from 0 to 8% by weight and in particular in amounts of from 0 to 5% by weight, in each case based on the total weight of the microemulsion.

The specified further ingredients for the microemulsion used according to the invention can, within the context of the invention, also be present as component E) in the cosmetic cleaning compositions.

Besides the specified further ingredients, the microemulsion and/or the cosmetic cleaning compositions which comprise the microemulsion can also comprise further customary cosmetic auxiliaries and additives which are known to the person skilled in the art, such as, for example, mild surfactants, emulsifiers, pearlescent waxes, stabilizers, salt, thickeners, consistency regulators, self-tanning agents, pigments, antioxidants, antidandruff agents, film formers, swelling agents, insect repellants, deodorant and antiperspirant active ingredients, biogenic active ingredients. Preferred biogenic active ingredients here are in particular tocopherol, tocopherol acetate, tocopherol palmitate, deoxyribonucleic acid, coenzyme Q10, ascorbic acid, retinol and retinyl derivatives, bisabolol, allantoin, phytantriol, panthenol, AHA acids, amino acids, ceramides, essential oils, hyaluronic acid, creatine, protein hydrolyzates, vegetable extracts, peptides and vitamin complexes.

The aqueous microemulsions according to the present description preferably have a pH between 2 and 9, where the ranges from 3 to 8 may be particularly advantageous.

Production of the Microemulsions

These emulsions are produced for example by firstly, in a first step, preparing a microemulsion comprising preferably at least 8-30% by weight of an alkyl (oligo)glycoside of the general formula $R^1O\text{-}[G]_p$ in which $R^1$ is an alkyl and/or alkenyl radical having 4 to 22 carbon atoms, G is a sugar radical having 5 or 6 carbon atoms and p is numbers from 1 to 10, and preferably 10-20% by weight of a cosurfactant and preferably 20-50% by weight of an oil body and the remainder to 100% by weight of water, and stirring this mixture, if necessary with heating to temperatures of 30 to 80° C.

In a preferred embodiment, the microemulsions are produced according to the teaching of WO 08/15507 A1: the process disclosed therein is a two-stage process in which, in the first step, a microemulsion is produced in a manner known per se. The microemulsions in step 1 are preferably produced by mixing the oil phase with the further oil-soluble ingredients, heating the oil phase to above the melting point of all of the constituents and then adding the aqueous surfactant-containing phase. The thermodynamically stable microemulsion is then formed spontaneously, with additional stirring if necessary.

According to the invention, the microemulsions are added to cleaning compositions known per se in order to improve the skin friendliness of these. Preferably, the microemulsions are added to cosmetic cleaning compositions, in particular shower gels. One advantage of the microemulsion to be used according to the invention is the ability to be able to stir these into the cleaning composition cold. This is a great advantage compared with wax-containing microemulsions or microemulsions which comprise solid fats. Cold within the context of the invention means room temperature, i.e. 20-25° C.

Depending on the requirement profile, the microemulsion is used directly.

Within the context of the invention, the microemulsion can be used with further additives as cosmetic cleaning composition.

Accordingly, a further subject matter of the invention is logically a cosmetic cleaning composition which comprises A) the microemulsion according to the invention. Furthermore, the cosmetic cleaning composition according to the invention comprises B) anionic surfactants, preferably alkoxylated, such as, for example, sodium lauryl ether sulfate,
C) cationic polymers,
D) optionally further surfactants,
E) optionally further cosmetic additives and
F) water.

The cosmetic cleaning compositions produced according to the invention in the form of finely divided emulsions can be used for producing cosmetic cleaning compositions, such as, for example, shower gels, shower baths, hair shampoos, hair lotions, foam baths, hand washing compositions, face cleaners, make-up removers, bath preparations, baby care products, creams, gels, lotions, alcoholic and aqueous/alcoholic solutions, emulsions, wax/fat masses, stick preparations, powders or ointments.

Preference is given to low viscosity, transparent to slightly cloudy gels for cleaning skin or hair.

The microemulsions and also the cosmetic cleaners can serve as impregnation medium for wipes, fabric, which are used wet or dry by the user or else are applied from a pump foamer.

The cosmetic cleaning compositions are prepared in a manner known per se. The microemulsions according to the above description are added to the ingredients of the cleaning compositions, the effect according to the invention only occurring when the finished microemulsion with all of the ingredients as intended is brought together with the remaining ingredients of the cleaning composition.

The addition of individual constituents does not lead to the desired result; what is essential here is the feature of the microemulsion for realizing the present teaching.

In a preferred embodiment, the cosmetic cleaning composition according to the invention comprises
A 0.1 to 20% by weight of a microemulsion to be used according to the invention
B 5-20% by weight of anionic surfactants
C 0.02-2% by weight of cationic polymers
D 0-15% by weight of further surfactants
E 0-8% by weight of cosmetic additives
F water ad 100% by weight.

In a further preferred embodiment, the cosmetic cleaning composition according to the invention consists of
A 0.1 to 20% by weight of a microemulsion to be used according to the invention
B 5-20% by weight of anionic surfactants
C 0.02-2% by weight of cationic polymers
D 0-15% by weight of further surfactants
E 0-8% by weight of cosmetic additives
F water ad 100% by weight.

Particular preference is given to a cosmetic cleaning composition comprising
A 0.2-10% by weight of a microemulsion to be used according to the invention
B 8-15% by weight of anionic surfactants
C 0.05-1% by weight of cationic polymers
D 0-5% by weight of further surfactants
E 0-5% by weight of cosmetic additives
F water ad 100% by weight.

As described above, as well as the microemulsion according to the invention, the cosmetic cleaning compositions according to the invention also comprise further components such as B) the anionic surfactants which are selected from the group which is formed from soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acryl tartrates, acyl glutamates and acyl aspartates, alkyl oligoglucoside sulfates, protein fatty acid condensates (in particular wheat-based vegetable products) and alkyl (ether) phosphates; particular preference is given here to the fatty alcohol ether sulfates, such as, for example, sodium lauryl ether sulfate or other compounds with comparable foaming behavior for use as cleaning care compositions such as shower gel, shampoo, hand washing composition or the like.

Cationic Polymers C)

As component C), the cosmetic compositions of the present patent application comprise cationic compound, in particular quaternary ammonium compounds or a cationic polymer. Quaternary ammonium compounds are understood here as meaning in particular quaternized fatty acid triethanolamine ester salts. Likewise of suitability, however, are alkylammonium halides.

Suitable cationic polymers are, for example, cationic cellulose derivatives, such as e.g. a quaternized hydroxyethylcellulose, cationic starch, copolymers of diallylammonium salts and acrylamides, quaternized vinylpyrrolidone/vinylimidazole polymers, such as e.g. Luviquat (BASF), condensation products of polyglycols and amines, quaternized collagen polypeptides, such as, for example, lauryldimonium hydroxypropyl hydrolyzed collagen (Lamequat), quaternized wheat polypeptides, polyethyleneimine, cationic silicone polymers, such as e.g. amidomethicones, copolymers of adipic acid and dimethylaminohydroxypropyldiethylenetriamine (Cartaretine), copolymers of acrylic acid with dimethyldiallylammonium chloride (Merquat 550), polyaminopolyamides, as described e.g. in FR-A 2252840, and also their crosslinked water-soluble polymers, cationic chitin derivatives, such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, quaternized ammonium salt polymers, such as e.g. Mirapol A-15, Mirapol AD-1, Mirapol AZ-1 from Miranol.

Further preferred cationic polymers are selected from the group of the homopolymers or copolymers of ester or amide derivatives of acrylic acid or methacrylic acid (e.g. INCI: Polyquaternium-7, or PQ-7), homopolymers of methacryloyl-ethyltrimethylammonium chloride (INCI: Polyquaternium-37, or PQ-37), quaternary copolymers of hydroxyethylcellulose and diallyldimethylammonium chloride (INCI: Polyquaternium-4, or PQ-4), polymeric quaternized ammonium salts of hydroxyethylcellulose modified with a trimethylammonium-substituted epoxide (INCI: Polyquaternium-10, or PQ-10), depolymerized guar gum derivatives which are quaternized (INCI: Guar Hydroxypropyl Trimonium Chloride) or quaternized guar derivatives and quaternary copolymers of hydroxyethyl-cellulose and diallyldimethylammonium chloride. In a preferred embodiment, the cationic polymer is selected from the group which is formed from Polyquaternium-7, Polyquaternium-10 and cationic guar derivatives.

Furthermore, cationic polymers according to the teaching of EP 1 767 554 A1, which are sold by the applicant under the name Polyquart Pro, can be used advantageously. The microemulsions according to the invention preferably comprise 0.05 to 2% by weight of these cationic polymers.

The preferred cationic polymers are selected from the group which is formed from Polyquaternium-7, Polyquaternium-10 and cationic guar derivatives. In a particularly preferred embodiment, preference is given to cationic guar derivatives since these are in keeping with the "green" concept.

Further Surfactants D)

As components D), the cosmetic compositions of the present patent application comprise further surfactants. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides or glucuronic acid derivatives, fatty acid N-alkylglucamides, protein hydrolyzates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of cationic surfactants are quaternary ammonium compounds, such as, for example, dimethyldistearylammonium chloride, and ester quats, in particular quaternized fatty acid trialkanolamine ester salts.

Within the context of the invention, preferred further surfactants are amphoteric or zwitterionic surfactants. Typical examples of amphoteric or zwitterionic surfactants are alkylbetains, alkylamidobetaines, aminopropionates, aminoglycinates, imidazoliniumbetaines and sulfobetaines, particular preference being given to cocamidopropylbetaine. The specified surfactants are exclusively known compounds. Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isothionates, fatty acid sarcosinates, fatty acid taurides, fatty acid glutamates, α-olefinsulfonates, ether carboxylic acids, alkyl oligoglucosides, fatty acid glucamides, alkylamidobetaines such as cocamidopropylbetaine, amphoacetate, such as sodium cocoamphoacetate and/or protein fatty acid condensates, the latter preferably based on wheat proteins.

Cosmetic Additives E

The further components E) of the cosmetic additives has already been described above. Within the context of the invention, it is preferred that the described cosmetic additives are present in the cosmetic cleaning composition and are not incorporated into the microemulsion. However, if the microemulsion is used without further components (B to E), it can comprise these additives. For the use as cleaning gel or as paste and ointment, consistency regulators and thickeners are preferably present as cosmetic additives. These can be selected from the following compounds:

Consistency Regulator and Thickener

Suitable consistency regulators are primarily fatty alcohols or hydroxy fatty alcohols having 12 to 22 and preferably 16 to 18 carbon atoms and in addition partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose and hydroxyethyl- and hydroxypropylcellulose, in addition relatively high molecular weight polyethylene glycol mono- and diesters of fatty acids, polyacrylates and hydrophobically modified polyacrylates, polyacrylamides, polymers, polyvinyl alcohol and polyvinylpyrrolidone. Bentonites which are a mixture of cyclopentasiloxane, disteardimonium hectorite and propylene carbonate have also proven to be particularly effective. Also of suitability are surfactants, such as, for example, ethoxylated fatty acid glycerides, esters of fatty acids with polyols, such as, for example, pentaerythritol or trimethylolpropane, fatty alcohol ethoxylates with narrowed homolog distribution or alkyl oligoglucosides, and also electrolytes such as sodium chloride and ammonium chloride.

If preservatives are used according to the invention these are preferably selected from the group which is formed from benzoic acid and salts thereof, citric acid and salts thereof, phenoxyethanol, benzyl alcohol, alkylparabens, preferably ethyl-, methyl- and propylparaben. Suitable preservatives are also, for example, formaldehyde solution, pentanediol or sorbic acid, and also the silver complexes known under the name Surfacine® and the other substance classes listed in Annex 6, Part A and B of the Cosmetics Ordinance.

By incorporating a microemulsion as component A) into the cosmetic cleaning compositions according to the invention, the transparent to slightly cloudy incorporation of relatively large amounts of oil bodies is possible, said oil bodies then, with the cationic polymers of component C) in the composition stabilized by the surfactants of component B), bringing about the exceptional conditioning properties of the preparation.

The application further provides the use of microemulsions according to the above description for improving the sensory properties of cosmetic cleaning compositions such as shower gel and hair shampoo.

Sensory properties are understood as meaning the properties of compositions which can lead to a change in sensory perception by people, thus in the present case is meant in particular the skin feel which is triggered by direct contact of the human skin with one substance or a substance mixture. In practice, this skin feel is ascertained e.g. by a panel test on subjects who qualify their sensory impressions in relation to certain parameters, such as "dryness of the skin", "softness of the skin" etc. by means of gradings.

By adding the microemulsions according to the invention to cleaning compositions, it is possible to improve the sensory impressions of the subjects following contact with the respective cleaning composition.

The microemulsions are preferably used in amounts of from 0.1 to 20% by weight, preferably from 0.2 to 10% by weight, based on the total weight of the cleaning composition, in order to achieve the desired success.

EXAMPLES

The three formulations H1-H3 were tested in a forearm test by test subjects. A comparison was carried out between H1 and H3. For this, the compositions were dripped onto the wetted forearm of the test subjects in a concentration of 10 g/l and left there for 30 seconds. The arm was then rinsed with water for 5 seconds. The test subjects were asked to assess their impressions for the areas "spreading of the composition", "softness following application", "softness after 30 minutes", "smoothness after application and after 30 minutes", "dryness after application and after 30 minutes" and "acceptance". Formulations H1 and H3 were tested against one another.

Here, it was found that formulation H3 was preferred over H1. H2 against H1 or H3 was not compared. In the properties: "softness of the skin after 30 minutes", "spreading of the shower gel on the skin" and "ability to be rinsed off", formulation H3 was assessed as significantly better than comparative formulation H1.

1. Formulations for Shower Gels

The formulations below are intended to illustrate the present invention without limiting it. Unless stated otherwise, all quantitative data, fractions and percentages are percentages by weight (% by wt.), based on the weight and the total amount or on the total weight of the preparations. The percentages by weight given in the examples are active content or % by wt. of active substance.

All of the substances are Cognis products. All substance names are registered trade marks.

The microemulsion according to the invention for cosmetic cleaning compositions—example formulation M1 to M5

TABLE 1

Microemulsion for cosmetic cleaning compositions, conductivity 0.5-1.0 mSi/cm, viscosities 2000-20 000 mPa s, pH = 3.2-4.5

| | | Active substance % by wt. | | | | |
|---|---|---|---|---|---|---|
| Substance | INCI | M1 | M2 | M3 | M4 | M5 |
| 1 Cetiol 88 | Caprylyl caprylate | 32.4 | 34.1 | 33.6 | 34.7 | 35.6 |
| 2 Plantacare 1200 UP | Lauryl glycoside | 18.5 | 18.0 | 17.5 | 17.5 | 17.0 |
| 3 Dehymuls PGPH | Polyglyceryl-2 dipolyhydroxystearate | 8.5 | 7.8 | 8.0 | 8.2 | 7.4 |
| 4 Lameform TGl | Polyglyceryl-3 diisostearate | 8.5 | 7.8 | 8.0 | 8.2 | 7.4 |
| 5 Glycerol | | 8.0 | 10.5 | 10.0 | 9.0 | 11.0 |
| Citric acid | | q.s | q.s | q.s | q.s | q.s |
| 6 Water | | ad 100 | ad 100 | ad 100 | ad 100 | ad 100 |

The microemulsions were prepared by mixing the components with stirring at a temperature of 75° C. The viscosity was determined using a Brookfield viscosimeter, spindle 2, at 20 rpm.

To produce the shower gels, one of the aforementioned microemulsions M1 to M5 (M2) was mixed into the following formulation in a further step. A transparent emulsion is formed.

TABLE 2

Shower gel formulations, H2 and H3 comprise the microemulsion, H1 serves as comparison formulation

| Substance | INCI | H1 | H2 | H3 |
|---|---|---|---|---|
| 1 Texapon N70 | Sodium laureth sulfate + 2EO | 14.3 | 14.3 | 14.3 |
| 2 Dehyton PK45 | Cocamidopropylbetaine | 5.0 | 5.0 | 5.0 |
| 3 Microemulsion M2 (as in Table 1) | | 0 | 2.0 | 4.0 |
| 4 Dehyquart Guar TC | Guar Hydroxypropyltrimonium chloride | 0.2 | 0.2 | 0.2 |
| 5 Arlypon TT | PEG-120-PPG-10-Trimethylolpropane Trioleate | 2.0 | 2.0 | 2.0 |
| 6 Dekafeld | DMDM Hydantoin | 0.2 | 0.2 | 0.2 |
| 7 NaCl | | 1.0 | 1.0 | 1.0 |
| 8 Water | | ad 100 | ad 100 | ad 100 |
| Deposition of caprylyl caprylate [µg/cm$^2$] | | 0.0 | 0.6 | 1.1 |

Deposition of Lipid Components on the Skin—Detection of Caprylyl Caprylate

Formulations 1 to 3 were investigated by test subjects as to their property of deposition of lipid components. The aim was to determine how the concentration on the skin of defined lipids after using the formulations according to the invention behaves compared to formulations without the microemulsion M1 to M5 described in the invention comprising more oil than water and glycerol as moisturizing agent. For this, the arms of the test subjects were prewashed with 13% strength Texapon NSO solution, a blank value was determined and the areas to be treated were divided up. 1 g of product was rubbed into the respective area by the test leader and then the area was rinsed with 950 ml of water in a defined manner. A glass cylinder was placed on flush, filled with 3 ml of ethanol and rubbed on the skin for 1 min using a glass rod. The eluates were transferred to vials by means of Pasteur pipette and analyzed by means of GC/MS coupling. The concentrations were given in µg/cm$^2$.

The results in the last column of Table 2 clearly show that by using the microemulsion according to the invention, a significantly higher deposition of the lipid component is recorded. These tests show which positive effects the microemulsion has on the skin. The negative effects of the washing-active substances, such as, for example, destruction of the lipid film on the skin and drying out of the skin, are cancelled out by using this microemulsion without, however, reducing or destroying the positive cleaning effects of the washing-active substances.

The invention claimed is:

1. A microemulsion comprising:
   (a) 15-25% by weight of at least one alkyl (oligo)glycoside,
   (b) 10-20% by weight of at least one cosurfactant different from (a),
   (c) 20-60% by weight of at least one non-water-soluble organic oil component,
   (d) 6-15% by weight of a moisturizing agent that is glycerol,
   (e) ad 100% by weight of water, and
   (f) 0-8% by weight of further ingredients;
   wherein the sum of (a) to (f) is 100% by weight.

2. The microemulsion according to claim 1, characterized in that the microemulsion comprises an alkyl (oligo)glycoside (a) according to the general formula R$^1$O-[G]p, in which R$^1$ is an alkyl and/or alkenyl radical having 4 to 22 carbon atoms, G is a sugar radical having 5 or 6 carbon atoms and p is numbers from 1 to 10.

3. The microemulsion according to claim 1 wherein cosurfactant (b) comprises one or more polyol fatty acid esters.

4. The microemulsion according to claim 1, wherein organic oil component (c) comprises one or more branched fatty alcohols, $C_6$-$C_{22}$-dialkyl ethers, ester oils, or mixtures thereof.

5. The microemulsion according to claim 4, wherein the organic oil component (c) comprises one or more ester oils that are selected from the group consisting of esters of linear $C_6$-$C_{22}$-fatty acids with linear or branched $C_6$-$C_{22}$-fatty alcohols, esters of branched $C_6$-$C_{13}$-carboxylic acids with linear or branched $C_6$-$C_{22}$-fatty alcohols, esters of linear $C_6$-$C_{22}$-fatty acids with branched alcohols, esters of $C_{18}$-$C_{38}$-alkylhydroxycarboxylic acids with linear or branched $C_6$-$C_{22}$-fatty alcohols, esters of linear and/or branched fatty acids with polyhydric alcohols and/or Guerbet alcohols, esters of $C_6$-$C_{22}$-fatty alcohols and/or Guerbet alcohols with aromatic carboxylic acids, esters of $C_2$-$C_{12}$-dicarboxylic acids with linear or branched alcohols having 1 to 22 carbon atoms or polyols having 2 to 10 carbon atoms and 2 to 6 hydroxyl groups, linear and branched $C_6$-$C_{22}$-fatty alcohol carbonates, wherein microemulsion is effective for producing a cosmetic cleaning composition.

6. The microemulsion according to claim 1, further comprising ingredients as component (f) that are selected from the group consisting of pH regulators, phenoxyethanol, UV photoprotective filters, antioxidants, biogenic active ingredients, perfume, dyes, biocides and preservatives, and alcohols.

7. A method for improving the sensory properties of a cosmetic cleaning composition, the method comprising forming a cosmetic cleaning composition from a microemulsion according to claim 1.

8. A cosmetic cleaning composition comprising:
A) a microemulsion according to claim 1,
B) at least one anionic surfactant,
C) at least one cationic polymer,
D) optionally further surfactants,
E) optionally cosmetic additives, and
F) water.

9. The cosmetic cleaning composition according to claim 8 comprising:
A) 0.1 to 20% by weight of the microemulsion according claims 1,
B) 5-20% by weight of at least one anionic surfactant,
C) 0.02-2% by weight of at least one cationic polymer,
D) 0-15% by weight of further surfactants,
E) 0-8% by weight of cosmetic additives, and
F) water ad 100% by weight,
with the proviso that the sum of A to F gives 100.

10. A method of delivering a cosmetic cleaning composition comprising:
obtaining the cosmetic cleaning composition according to claim 8; and
including the cosmetic cleaning composition in wipes, shower gels, shower baths, hair shampoos, hair lotions, foam baths, hand washing compositions, face cleaning compositions, make-up removers, bath preparations, baby care products, creams, gels, lotions, alcoholic and aqueous/alcoholic solutions, emulsions, wax/fat masses, stick preparations, powders, or ointments.

11. The microemulsion according to claim 4, wherein the organic oil component comprises one or more esters of branched or linear monocarboxylic acids having 6 to 22 carbon atoms with linear or branched fatty alcohols having 6 to 22 carbon atoms, hydrocarbons, or mixtures thereof.

12. The microemulsion according to claim 5, wherein the one or more ester oils comprise isopropyl palmitate, isopropyl myristate, ethylhexyl palmitate, cetyl palmitate, myristyl myristate, oleyl oleate, ethylhexyl stearates, di-n-octyl carbonates, oleyl oleate, caprylyl caprylate, oleyl erucate, or mixtures thereof.

13. The microemulsion according to claim 6, wherein the pH regulator comprises citric acid and/or the alcohol comprises ethanol, isopropanol, propanol, or combinations thereof.

* * * * *